United States Patent [19]

Kawai et al.

[11] Patent Number: 4,747,875
[45] Date of Patent: May 31, 1988

[54] CHROMOGENIC AZAPHTHALIDE COMPOUND AND A COLOUR-FORMING RECORDING COMPOSITION CONTAINING THE SAME

[75] Inventors: Hajime Kawai, Tsuzuki; Toshiyuki Nakai; Katsuhiko Tsunemitsu, both of Kyoto, all of Japan

[73] Assignee: Yamada Chemical Co., Ltd., Kyoto, Japan

[21] Appl. No.: 67,395

[22] Filed: Jun. 26, 1987

Related U.S. Application Data

[63] Continuation of Ser. No. 658,997, Oct. 9, 1984, abandoned.

[30] Foreign Application Priority Data

Oct. 18, 1983 [JP] Japan ................... 58-195448

[51] Int. Cl.$^4$ .............................................. C09D 11/00
[52] U.S. Cl. ..................... 106/21; 503/218; 427/151
[58] Field of Search ................ 106/21; 503/218; 427/151

[56] References Cited

U.S. PATENT DOCUMENTS

| | | | |
|---|---|---|---|
| 3,775,424 | 11/1973 | Farber | 260/295 B |
| 3,853,869 | 12/1974 | Farber | 260/250 BC |
| 4,046,776 | 9/1977 | Garner et al. | 544/58 |
| 4,275,905 | 6/1981 | Miller | 106/14.5 |
| 4,299,411 | 11/1981 | Brockett | 8/636 |

FOREIGN PATENT DOCUMENTS

| | | |
|---|---|---|
| 0082822 | 12/1982 | European Pat. Off. . |
| 0140833 | 5/1985 | European Pat. Off. . |
| 2002047 | 9/1970 | Fed. Rep. of Germany . |
| 2163658 | 7/1972 | Fed. Rep. of Germany . |
| 2218895 | 12/1972 | Fed. Rep. of Germany . |
| 2423534 | 12/1974 | Fed. Rep. of Germany . |
| 2424935 | 12/1974 | Fed. Rep. of Germany . |
| 2423533 | 12/1974 | Fed. Rep. of Germany . |
| 2758771 | 7/1978 | Fed. Rep. of Germany . |
| 2808798 | 9/1978 | Fed. Rep. of Germany . |
| 2919421 | 11/1979 | Fed. Rep. of Germany . |
| 2257711 | 7/1980 | Fed. Rep. of Germany . |
| 3008494 | 9/1980 | Fed. Rep. of Germany . |
| 3008475 | 9/1980 | Fed. Rep. of Germany . |
| 2937525 | 3/1981 | Fed. Rep. of Germany . |
| 5116 | 1/1975 | Japan . |
| 38243 | 10/1976 | Japan . |
| 2006248 | 5/1979 | United Kingdom . |
| 2031934 | 4/1980 | United Kingdom . |
| 2103234 | 2/1983 | United Kingdom . |

*Primary Examiner*—Amelia Burgess Yarbrough
*Attorney, Agent, or Firm*—Cushman, Darby & Cushman

[57] ABSTRACT

Disclosed herein is a chromogenic compound of the formula:

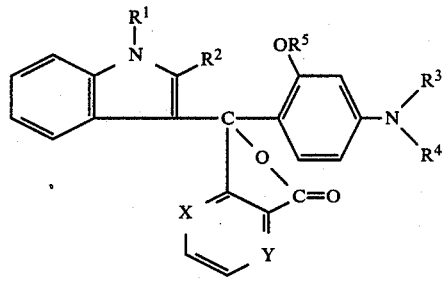

wherein $R^1$, $R^2$, $R^3$ and $R^4$ respectively represent an alkyl group having 1 to 4 carbon atoms; $R^5$ represents an alkyl group having 5 to 8 carbon atoms or a cycloalkyl group having 5 to 7 carbon atoms; one of X and Y represents a nitrogen atom and the other of X and Y represents a carbon atom, and a color-forming recording composition containing at least one of the chromogenic compounds.

17 Claims, No Drawings

CHROMOGENIC AZAPHTHALIDE COMPOUND AND A COLOUR-FORMING RECORDING COMPOSITION CONTAINING THE SAME

This is a continuation of application Ser. No. 658,997, filed Oct. 9, 1984, which was abandoned upon the filing hereof.

DESCRIPTION OF THE INVENTION

The present invention relates to novel chromogenic azaphthalide compounds and a recording material such as pressure-sensitive copying paper or heat-sensitive recording paper having the novel azaphthalide compounds represented by the formula(I):

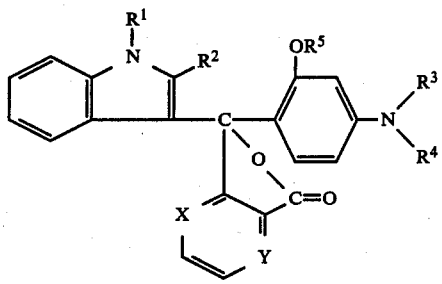

wherein $R^1$, $R^2$, $R^3$ and $R^4$ represent respectively alkyl group of 1 to 4 carbon atoms; $R^5$ represents alkyl group of 5 to 8 carbon atoms or cycloalkyl group of 5 to 7 carbon atoms; one of X and Y represents nitrogen atom and the other of X and Y represents carbon atom.

The azaphthalide compound represented by the formula(I) (hereinafter referred to as the present compounds) has been newly synthesized by the present inventors. The present compounds are substantially colorless and have a property of quickly giving blue or blue-violet color development by closely contacting one of the present compounds with an active clay substance such as activated clay, acid clay, attapulgite clay, bentonite, kaoline and the like or an organic acid substance such as phenol, cresol, naphthol, 4,4'-isopropylidenediphenol (Bisphenol A), methyl hydroxybenzoate, benzyl hydroxybenzoate, 4,4'-dihydroxydiphenylsulfone, 4-hydroxy-4'-methyldiphenylsulfone, a metal salt of salicylic acid, phenolformaldehyde resin and the like. In addition, the present compounds easily dissolve in organic solvents.

As a compound hitherto known to give blue or blue-violet color development, diphenylmethane derivatives and triphenylmethane derivatives, phthalide compounds and leucomethylene blues may be mentioned. However, each compound has a insufficient property. 4,4'-Bis(dimethylamino)benzhydrol(Michler's hydrol) which is one of the diphenylmethane derivatives, is poor in stability before developing the color. Further, in the case where an organic substance such as phenol-formaldehyde is used as a color-developer, 4,4'-bis(dimethylamino)benzhydrol is inferior in developability. Furthermore, the light-stability of the developed color image is also poor.

4,4',4''-Tris(dimethylamino)triphenylmethane (leucocrystal violet) which is one of the triphenylmethane derivatives is unstable in itself and is apt to be colored before color development. Although 3,3-bis-(p-dimethylaminophenyl)-6-dimethylaminophthalide(crystalviolet lactone, CVL) develops quickly into a deep blue-violet color, the light-stability of the developed color image is poor. Although 3,7-(dimethylamino)-10-benzoylphenothazine(benzoylleucomethylene blue (BLMB)) which is one of the leucomethylene blues, develops an extremely light-stable image, a color developing is very slow. Further, in the case where an organic color developer is used, BLMB is insufficient in developing property.

In addition, although 3-(4-diethylamino-2-ethoxyphenyl)-3-(1-ethyl-2-methyl-indol-3-yl)-4-azaphthalide, 3-(4-diethylamino-2-ethoxyphenyl)-3-(1-ethyl-2-methyl-3-indolyl)-7-azaphthalide and the like are known as a similar compound to the compound represented by the formula(I), they have insufficient properties such as a low solubility in a solvent. Further, they tend to occur a development during microcapsulation or during preparing heat-sensitive recording paper.

The novel azaphthalide compounds according to the present invention have been devised to improve the insufficiency of the conventional color formers. The compounds of the present invention are highly valuable as a color former for use in pressure-sensitive copying paper and heat-sensitive recording paper.

The novel azaphthalide compound according to the present invention can be singly used as a color former and any mixture of more than one of the novel azaphthalide compounds according to the present invention can be used for the same purpose. In addition, any mixture of the novel azaphthalide compound(s) and one or more than one of the known color formers can be also used for the same purpose. As the known color former which can be used together with one of the novel azaphthalide compounds according to the present invention, for instance, 3,3-bis(aminophenyl)phthalide, 3,3-bis(indolyl)phthalide, 3-aminofluoran, 2,6-diaminofluoran, spiropyran, triarylmethane, phenoxazine, phenothiazine, chromenopyrazole, chromenoindole and the like may be mentioned.

As the solvent used for dissolving the color former in the preparation of pressure-sensitive copying papers, alkylnaphthalene, diarylethane, hydrogenated terphenyl, alkylbiphenyl and the like may be mentioned.

The color former dissolved in a solvent is emulsified or capsulated in a binder and then, the emulsified or capsulated color former is painted onto a sheet of paper. As a method for encapsulating the solution of the novel azaphthalide, a method of coacervation or a method of interfacial polymerization may be adopted. The heat-sensitive recording papers are prepared by pulverizing the color former together with an organic color developer and painting the resultant mixture onto a sheet of paper together with the binder. In general, low-melting compounds are used as a sensitizer and, for example, waxes, amides, esters, ethers, sulfonamides, and amines may be mentioned. In the present invention, those compounds are used as a sensitizer for preparing a heat-sensitive recording paper according to the present invention.

In order to clarify the excellent properties of the novel azaphthalide compounds according to the present invention, results of comparative tests are set forth below.

The comparative tests of the following present compounds (A) to (G) and the following known compounds (H) and (I) have been carried out.

The present compound (A)

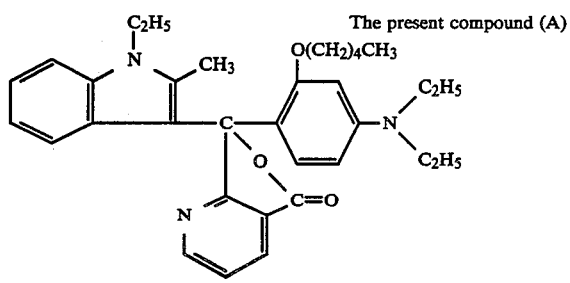

3-(4-diethylamino-2-n-pentyloxyphenyl)-3-
(1-ethyl-2-methylindol-3-yl)-4-azaphthalide.

The present compound (B)

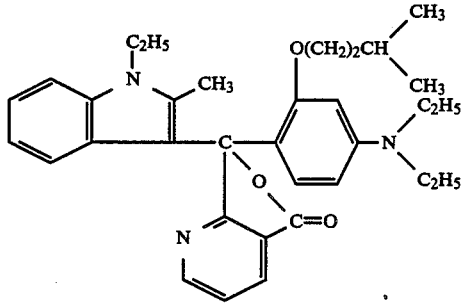

3-(4-diethylamino-2-iso-pentyloxyphenyl)-3-
(1-ethyl-2-methylindol-3-yl)-4-azaphthalide.

The present compound (C)

3-(4-diethylamino-2-n-hexyloxyphenyl)-3-
(1-ethyl-2-methylindol-3-yl)-4-azaphthalide.

The present compound (D)

3-(4-diethylamino-2-cyclopentyloxyphenyl)-3-
(1-ethyl-2-methylindol-3-yl)-4-azaphthalide.

The present compound (E)

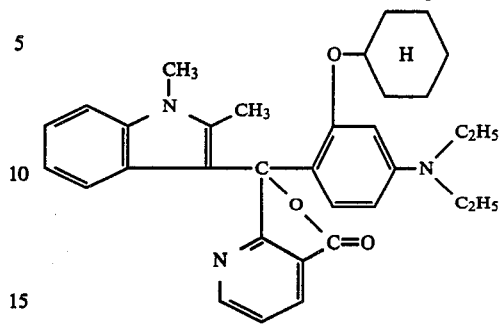

3-(4-diethylamino-2-cyclohexyloxyphenyl)-3-
(1,2-dimethylindol-3-yl)-4-azaphthalide.

The present compound (F)

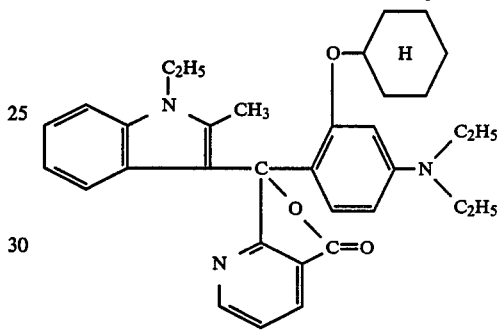

3-(4-diethylamino-2-cyclohexyloxyphenyl)-3-
(1-ethyl-2-methylindol-3-yl)-4-azaphthalide.

The present compound (G)

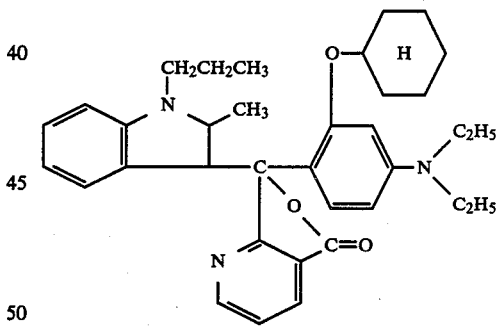

3-(4-diethylamino-2-cyclohexyloxyphenyl)-3-
(1-n-propyl-2-methylindol-3-yl)-4-azaphthalide.

The known compound (H)

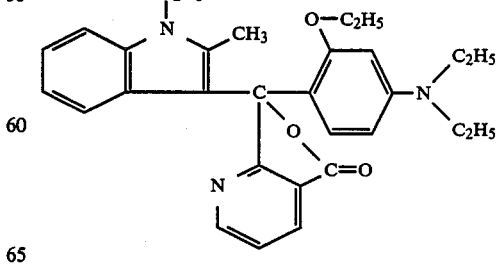

3-(4-diethylamino-2-ethoxyphenyl)-3-
(1-ethyl-2-methylindol-3-yl)-4-azaphthalide -continued

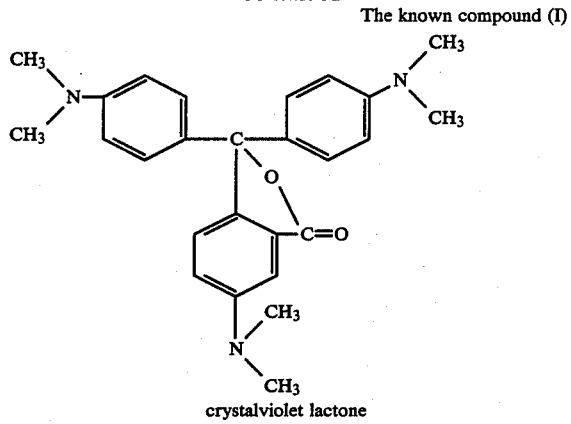

The known compound (I)

crystalviolet lactone

Test 1

Solubility in a solvent for preparing pressure-sensitive recording paper:

The solubility of the respective test compounds into KMC 113 (a solvent of alkylnaphthalene used for a pressure-sensitive recording paper, made by Kureha Chem. Ind. Co., Ltd.) at 25° C. was determined and was shown below.

| Compound | The present compound | | | | | | | The known compound | |
|---|---|---|---|---|---|---|---|---|---|
| | A | B | C | D | E | F | G | H | I |
| Solubility (% by weight) | >7 | >5 | >5 | 5 | 5 | >7 | >7 | 1.5 | 2.5 |

As seen above, the azaphthalide compounds (A) to (G) of the present invention are highly soluble in a solvent for use in preparing pressure-sensitive recording papers and are profitable in preparing thereof.

Test 2

Light-stability of the developed color image:

7 g of each of the compounds (A) to (G) and the known compounds (H) and (I) was dissolved in 93 ml of KMC 113 and the thus prepared solutions were respectively microcapsuled by the method of Preparation Example 1 described below. The obtained microcapsules were coated on a sheet of paper to prepare an upper sheet in which the amount of the color former was 0.15g/m² of the surface area of the sheet. The obtained upper sheet was piled onto a lower sheet to which a phenol-formaldehyde resin had been coated and a pressure was applied on the piled sheets to develop a color image. The each developed color image was exposed to sunlight for a time period shown in Tables 1 and 2. Thereafter, the reflection color density of the color image was measured by a reflection densitometer (a model RD-514 made by Macbeth Co.), while using Wratten filter #25.

The results are shown in Tables 1 and 2.

TABLE 1

| | | Reflection color density | | |
|---|---|---|---|---|
| | | Time period of exposure (hour) | | |
| Compound | | 0 | 2 | 4 |
| The | A | 1.00 | 0.98 | 0.94 |

TABLE 1-continued

| | | Reflection color density | | |
|---|---|---|---|---|
| | | Time period of exposure (hour) | | |
| Compound | | 0 | 2 | 4 |
| present compound | B | 1.01 | 0.98 | 0.95 |
| | C | 0.99 | 0.97 | 0.94 |
| The known compound | I | 1.05 | 0.92 | 0.75 |

TABLE 2

| | | Reflection color density | | |
|---|---|---|---|---|
| | | Time period of exposure (hour) | | |
| Compound | | 0 | 6 | 18 |
| The present compound | D | 0.98 | 0.95 | 0.85 |
| | E | 1.00 | 0.96 | 0.85 |
| | F | 0.95 | 0.91 | 0.82 |
| | G | 0.97 | 0.90 | 0.81 |
| The known compound | H | 1.05 | 0.88 | 0.58 |

As are seen above, the degree of discoloration of the color images formed by the azaphthalide of the present invention due to exposure to sunlight was remarkably small as compared to those of the known compounds (H) and (I). The results show that the light-stability of the pressure-sensitive recording papers and the heat-sensitive recording papers according to the present invention is excellent.

Test 3

Spontaneous Color Forming Property

Spontaneous color forming property was determined by dissolving each compound in a dilute aqueous solution of an acid.

In a vessel, 10 ml of 15wt % aqueous acetic acid solution (that is, a mixture of 15 weight % of acetic acid and 85 weight % of water) was added to 15 ml of the 3 wt % toluene solution of each of the present compounds (A) to (G) and the know compound (H) and then, the resultant mixture was shaked vigorously for one minute. Thereafter, the mixture was left to stand still and the separated aqueous layer was collected. The absorbance of the aqueous solution was determined at 581 nm or 580 nm by a spectrophotometer (model UV-200, made bY SHIMADZU CORPORATION). The absorbance of the aqueous solution concerning the known compound (H) was very high and therefore, the aqueous solution concerning the known compound (H) was diluted with 15 wt % aqueous acetic acid solution to ten times and the diluted aqueous solution was determined.

The results are shown in Table 3.

TABLE 3

| Com- pound | The present compound | | | | | | | The known compound |
|---|---|---|---|---|---|---|---|---|
| | A | B | C | D | E | F | G | H |
| Absor- bance | 0.72 | 0.71 | 0.51 | 0.75 | 0.74 | 0.70 | 0.50 | 0.64 |

As seen in Table 3, the coloration of the novel azaphthalide of the present invention with the dilute aqueous solution of acetic acid was remarkably slight as compared to the known azaphthalide compound (H). In the case of preparing the pressure-sensitive recording paper, an acid is added to adjust the pH of the microcapsuling preparation and the above-mentioned fact shows that the coloration by the added acid is extremely slight when the novel azaphthalide of the present invention is used in the preparation of the pressure-sensitive recording paper. In addition, the above-mentioned fact also shows that in the case of preparing heat-sensitive recording papers, the spontaneous color development (so-called fog) occurring at the time of admixing an organic color developer such as bisphenol A is slight enough to obtain a white paper product.

The novel azaphthalide represented by the formula (I) according to the present invention can be synthesized in one of the following two synthetic routes.

Synthetic Route 1

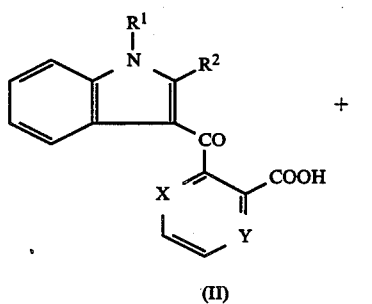

(II)

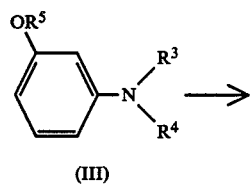

(III)

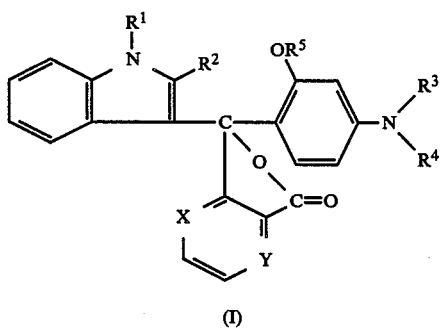

(I)

Synthetic Route 2

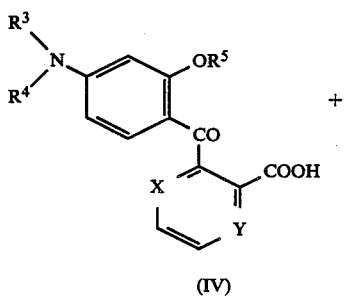

(IV)

-continued
Synthetic Route 1

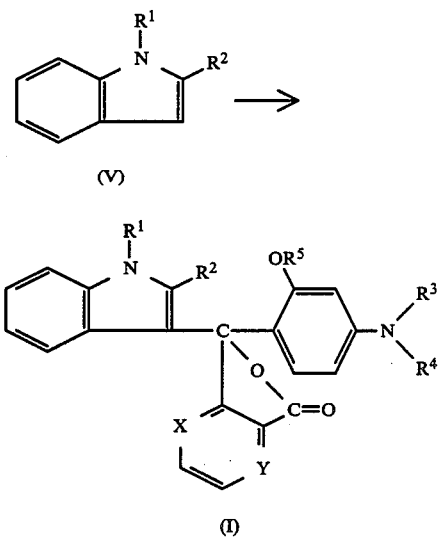

(V)

(I)

In the synthetic route 1, 1.0 part by mol of a derivative of pyridinecarboxylic acid represented by the formula (II) is reacted with 1.0 part by mole of a derivative of m-dialkylaminophenol represented by the formula (III) in the presence of a dehydrating, condensing agent such as conc. sulfuric acid, acetic anhydride, polyphosphoric acid and the like at a temperature of 10° to 100° C.

In the synthetic route 2, 1.0 part by mol of a derivative of pyridinecarboxylic acid represented by the formula (IV) is reacted with 1.0 part by mol of a derivative of indole represented by the formula (V) in the presence of the dehydrating, condensing agent at a temperature of 10° to 100° C. The synthetic route 1 is more preferable than the synthetic route 2.

The derivative of pyridinecarboxylic acid represented by the formula (II) is prepared by reacting anhydrous quinolinic acid with a derivative of indole represented by the formula (V) in an organic solvent such as benzene, toluene, tetrachloroethane, chlorobenzene, nitrobenzene and the like, or in the presence of a Friedel-Crafts catalyst. The obtained derivative of pyridinecarboxylic acid represented by the formula (II) is a mixture of the following two isomers (IIa) and (IIb). The mixture may be used in the next step as it is or, if necessary, one of the isomers may be used after separating the mixture into each isomer.

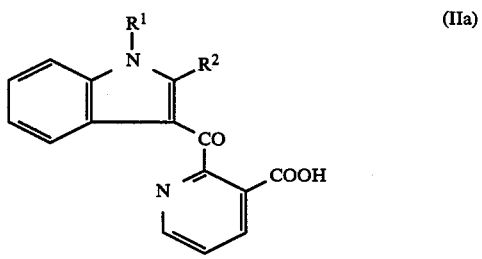

(IIa)

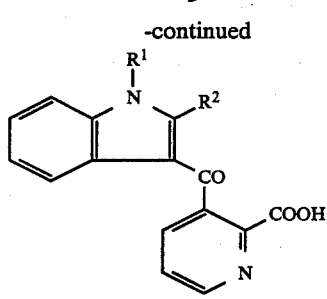

The derivative of pyridinecarboxylic acid (IV) is prepared by reacting quinolinic acid anhydride with a derivative of m-dialkylaminophenol represented by the formula (III) as above. Also, the obtained derivative of pyridinecarboxylic acid represented by the formula (IV) is a mixture of the following two isomers (IVa) and (IVb) and the mixture may be used in the next step as it is, or if necessary, one of the isomers may be used after separating the mixture into each isomer.

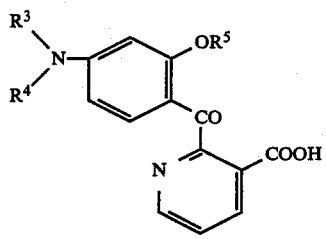

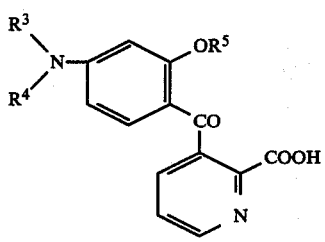

The azaphthalide compounds represented by the formula (I) according to the present invention are crystals of almost colourless and show the absorption maxima in the range of 580 to 582 nm in an aqueous 95% by weight solution of acetic acid and as the concrete example thereof, the following compounds may be mentioned:

The present invention includes two isomers of azaphthalide namely, 4-azaphthalide and 7-azaphthalide. For convenience of explanation, the isomers are denoted by (4/7)-azaphthalide.

3-(4-dimethylamino-2-n-pentyloxyphenyl)-3-(1,2-dimethylindol-3-yl)-(4/7)-azaphthalide,
3-(4-dimethylamino-2-iso-pentyloxyphenyl)-3-(1,2-dimethylindol-3-yl)-(4/7)-azaphthalide,
3-(4-dimethylamino-2-n-hexyloxyphenyl)-3-(1,2-dimethylindol-3-yl)-(4/7)-azaphthalide,
3-(4-dimethylamino-2-n-pentyloxyphenyl)-3-(1-ethyl-2-methylindol-3-yl)-(4/7)-azaphthalide,
3-(4-dimethylamino-2-iso-pentyloxyphenyl)-3-(1-ethyl-2-methylindol-3-yl)-(4/7)-azaphthalide,
3-(4-dimethylamino-2-n-hexyloxyphenyl)-3-(1-ethyl-2-methylindol-3-yl)-(4/7)-azaphthalide,
3-(4-diethylamino-2-n-pentyloxyphenyl)-3-(1,2-dimethylindol-3-yl)-(4/7)-azaphthalide,
3-(4-diethylamino-2-isopentyloxyphenyl)-3-(1,2-dimethylindol-3-yl)-(4/7)-azaphthalide,
3-(4-diethylamino-2-n-hexyloxyphenyl)-3-(1,2-dimethylindol-3-yl)-(4/7)-azaphthalide,
3-(4-diethylamino-2-n-heptyloxyphenyl)-3-(1,2-dimethylindol-3-yl)-(4/7)-azaphthalide,
3-(4-diethylamino-2-n-octyloxyphenyl)-3-(1,2-dimethylindol-3-yl)-(4/7)-azaphthalide,
3-(4-diethylamino-2-n-pentyloxyphenyl)-3-(1-ethyl-2-methylindol-3-yl)-(4/7)-azaphthalide,
3-(4-diethylamino-2-isopentyloxyphenyl)-3-(1-ethyl-2-methylindol-3-yl)-(4/7)-azaphthalide,
3-(4-diethylamino-2-n-hexyloxyphenyl)-3-(1-ethyl-2-methylindol-3-yl)-(4/7)-azaphthalide,
3-(4-diethylamino-2-n-heptyloxyphenyl)-3-(1-ethyl-2-methylindol-3-yl)-(4/7)-azaphthalide,
3-(4-diethylamino-2-n-octyloxyphenyl)-3-(1-ethyl-2-methylindol-3-yl)-(4/7)-azaphthalide,
3-(4-diethylamino-2-n-hexyloxyphenyl)-3-(1,2-diethylindol-3-yl)-(4/7)-azaphthalide,
3-(4-diethylamino-2-n-pentyloxyphenyl)-3-(1-n-propyl-2-methylindol-3-yl)-(4/7)-azaphthalide,
3-(4-diethylamino-2-iso-pentyloxyphenyl)-3-(1,2-di-n-propylindol-3-yl)-(4/7)-azaphthalide,
3-(4-diethylamino-2-n-pentyloxyphenyl)-3-(1-n-butyl-2-methylindol-3-yl)-(4/7)-azaphthalide,
3-(4-diethylamino-2-iso-pentyloxyphenyl)-3-(1,2-di-n-butylindol-3-yl)-(4/7)-azaphthalide,
3-(4-di-n-propylamino-2-n-pentyloxyphenyl)-3-(1,2-dimethylindol-3-yl)-(4/7)-azaphthalide,
3-(4-di-n-propylamino-2-isopentyloxyphenyl)-3-(1,2-dimethylindol-3-yl)-(4/7)-azaphthalide,
3-(4-di-n-propylamino-2-n-hexyloxyphenyl)-3-(1,2-dimethylindol-3-yl)-(4/7)-azaphthalide,
3-(4-di-n-butylamino-2-n-pentyloxyphenyl)-3-(1,2-dimethylindol-3-yl)-(4/7)-azaphthalide,
3-(4-di-iso-butylamino-2-iso-pentyloxyphenyl)-3-(1,2-dimethylindol-3-yl)-(4/7)-azaphthalide,
3-(4-di-n-butylamino-2-n-hexyloxyphenyl)-3-(1,2-dimethylindol-3-yl)-(4/7)-azaphthalide,
3-(4-dimethylamino-2-cyclopentyloxyphenyl)-3-(1,2-dimethylindol-3-yl)-(4/7)-azaphthalide,
3-(4-dimethylamino-2-cyclohexyloxyphenyl)-3-(1,2-dimethylindol-3-yl)-(4/7)-azaphthalide,
3-(4-dimethylamino-2-cycloheptyloxyphenyl)-3-(1,2-dimethylindol-3-yl)-(4/7)-azaphthalide,
3-(4-dimethylamino-2-cyclopentyloxyphenyl)-3-(1-ethyl-2-methylindol-3-yl)-(4/7)-azaphthalide,
3-(4-dimethylamino-2-cyclohexyloxyphenyl)-3-(1-ethyl-2-methylindol-3-yl)-(4/7)-azaphthalide,
3-(4-dimethylamino-2-cycloheptyloxyphenyl)-3-(1-ethyl-2-methylindol-3-yl)-(4/7)-azaphthalide,
3-(4-diethylamino-2-cyclopentyloxyphenyl)-3-(1,2-dimethylindol-3-yl)-(4/7)-azaphthalide,
3-(4-diethylamino-2-cyclohexyloxyphenyl)-3-(1,2-dimethylindol-3-yl)-(4/7)-azaphthalide,
3-(4-diethylamino-2-cycloheptyloxyphenyl)-3-(1,2-dimethylindol-3-yl)-(4/7)-azaphthalide,
3-(4-diethylamino-2-cyclopentyloxyphenyl)-3-(1-ethyl-2-methylindol-3-yl)-(4/7)-azaphthalide, 3-(4-diethylamino-2-cyclohexyloxyphenyl)-3-(1-ethyl-2-methylindol-3-yl)-(4/7)-azaphthalide,
3-(4-diethylamino-2-cycloheptyloxyphenyl)-3-(1-ethyl-2-methylindol-3-yl)-(4/7)-azaphthalide,
3-(4-diethylamino-2-cyclohexyloxyphenyl)-3-(1,2-diethylindol-3-yl)-(4/7)-azaphthalide,
3-(4-diethylamino-2-cyclohexyloxyphenyl)-3-(1-n-propyl-2-methylindol-3-yl)-(4/7)-azaphthalide, 3-(4-diethylamino-2-cyclohexyloxyphenyl)-3-(1,2-di-n-propylindol-3-yl)-(4/7)-azaphthalide,
3-(4-diethylamino-2-cyclohexyloxyphenyl)-3-(1-n-butyl-2-methylindol-3-yl)-(4/7)-azaphthalide,
3-(4-diethylamino-2-cyclohexyloxyphenyl)-3-(1,2-di-n-butylindol-3-yl)-(4/7)-azaphthalide,
3-(4-di-n-propylamino-2-cyclopentyloxyphenyl)-3-(1,2-dimethylindol-3-yl)-(4/7)-azaphthalide,
3-(4-di-n-propylamino-2-cyclohexyloxyphenyl)-3-(1-ethyl-2-methylindol-3-yl)-(4/7)-azaphthalide,
3-(4-di-n-propylamino-2-cycloheptyloxyphenyl)-3-(1,2-dimethylindol-3-yl)-(4/7)-azaphthalide,
3-(4-di-n-butylamino-2-cyclohexyloxyphenyl)-3-(1,2-dimethylindol-3-yl)-(4/7)-azaphthalide,
3-(4-di-iso-butylamino-2-cyclohexyloxyphenyl)-3-(1,2-dimethylindol-3-yl)-(4/7)-azaphthalide, and
3-(4-di-n-butylamino-2-cyclohexyloxyphenyl)-3-(1-ethyl-2-methylindol-3-yl)-(4/7)-azaphthalide.

The process for preparing the azaphthalide compounds according to the present invention will be concretely explained while referring to the following synthetic examples.

SYNTHETIC EXAMPLE 1

Synthesis of
3-(4-diethylamino-2-n-pentyloxyphenyl)-3-(1-ethyl-2-methylindol-3-yl)-4-azaphthalide.

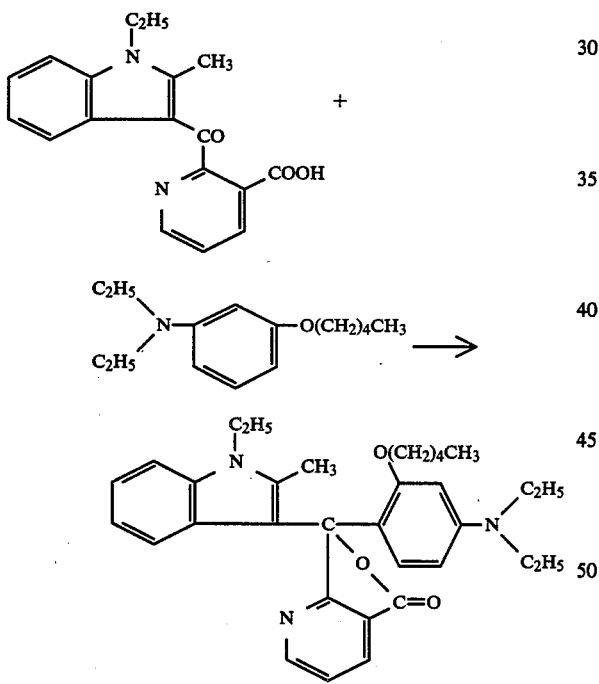

Into 150 ml of acetic anhydride, 15.4 g of (1-ethyl-2-methylindol-3-yl) (3-carboxypyridin-2-yl) ketone and 12.9 g of 1-n-pentyloxy-3-diethylaminobenzene were added, and the resultant mixture was stirred for 5 hours at 50° to 60° C. After cooling the reaction mixture to room temperature, the cooled mixture was poured into 1000 g of iced water to hydrolyze acetic anhydride. Thereafter, an aqueous diluted solution of sodium hydroxide was added to the mixture to adjust the pH of the mixture to 11 to 12. After adding 200 ml of toluene to the resultant mixture and stirring under heating, the toluene layer was collected and 1 g of activated carbon was added to the toluene solution. After heating the toluene solution and filtering thereof at 80° C., toluene was distilled off from the toluene solution. Thereafter, 150 ml of methanol was added to the distillation residue. The mixture was stirred and was filtered. The residue was dried and as a result, 21.0 g of 3-(4-diethylamino-2-n-pentyloxyphenyl)-3-(1-ethyl-2-methylindol-3 melting at 157° to 159° C. was obtained as pale blue crystals. The elementary analytical data of the product were as follows.

|  | C (%) | H (%) | N (%) |
|---|---|---|---|
| Calculated | 75.40 | 7.48 | 7.99 |
| Found | 74.72 | 7.53 | 7.92 |

By the way, (1-ethyl-2-methylindol-3-yl) (3-carboxypyridin-2-yl) ketone used herein had been synthesized as follows.

Into 50 ml of toluene, 14.9 g of quinolinic anhydride and 15.9 g of 1-ethyl-2-methylindole were added, and the resultant mixture was stirred for 5 hours at 70° C. Thereafter, the mixture was cooled to room temperature and precipitates were collected by filtration and the collected precipitates were dried and as a result, an isomeric mixture of the object compound was obtained in yield of 26.2 g. By recrystallizing the mixture from an organic solvent, (1-ethyl-2-methylindol-3-yl) (3-carboxypyridin-2-yl) ketone which did not contain its isomer was obtained. The product was pale brown and melting point thereof was 178° to 179° C.

SYNTHETIC EXAMPLE 2

Synthesis of a mixture of
3-(4-diethylamino-2-isopentyloxyphenyl)-3-(1-ethyl-2-methylindol-3-yl)-4-azaphthalide and
3-(4-diethylamino-2-iso-pentyloxyphenyl)-3-(1-ethyl-2-methylindol-3-yl)-7-azaphthalide

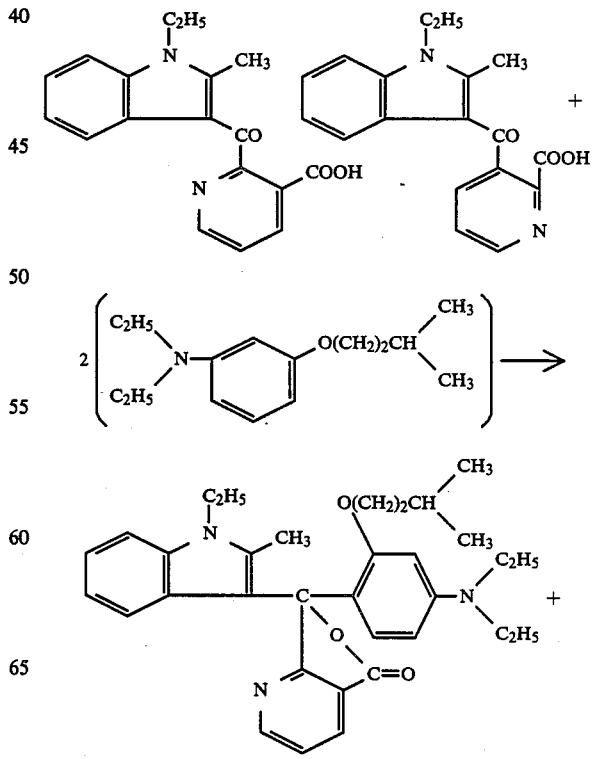

-continued

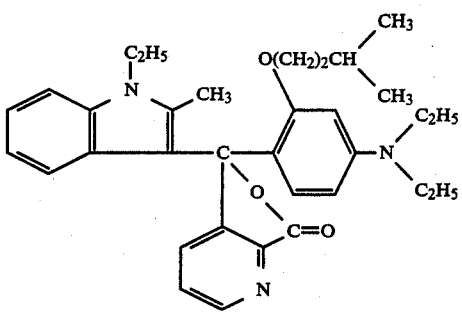

3-yl) (3-carboxypyridin-2-yl) ketone and (1-ethyl-2-methylindol-3-yl) (2-carboxypyridin-3-yl) ketone and 12.9 g of 1-isopentyloxy-3-diethylaminobenzene, 19.5 g of a mixture of the objective compounds melting at 148° to 152° C. was obtained as pale yellow crystals. The elementary analytical data of the product were as follows.

|  | C (%) | H (%) | N (%) |
|---|---|---|---|
| Calculated | 75.40 | 7.48 | 7.99 |
| Found | 74.87 | 7.54 | 8.04 |

SYNTHETIC EXAMPLE 3

Synthesis of 3-(4-diethylamino-2-n-hexyloxyphenyl)-3-(1-ethyl-2-methylindol-3-yl)-4-azaphthalide

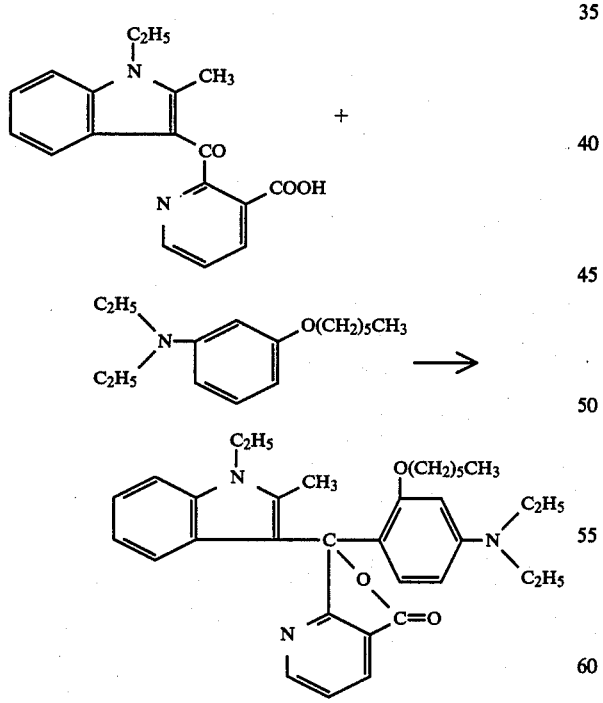

Into 200 ml of acetic anhydride, 15.4 g of (1-ethyl-2-methylindol-3-yl) (3-carboxypyridin-2-yl) ketone and 13.7 g of 1-n-hexyloxy-3-diethylaminobenzene were added, and the resultant mixture was stirred for 3 hours to 60° to 65° C. After cooling the reaction mixture to room temperature, the cooled reaction mixture was treated by the same manner as in Synthetic Example 1 and as a result, 18.9 of the objective compound of the melting point of 154° to 156° C. as pale blue crystals was obtained. The elementary analytical data of the product were as follows.

|  | C (%) | H (%) | N (%) |
|---|---|---|---|
| Calculated | 75.67 | 7.66 | 7.79 |
| Found | 76.12 | 7.58 | 7.86 |

SYNTHETIC EXAMPLE 4

Synthesis of a mixture of 3-(4-diethylamino-2-n-pentyloxyphenyl)-3-(1,2-dimethylindol-3-yl)-4-azaphthalide and 3-(4-diethylamino-2-n-pentyloxyphenyl)-3-(1,2-dimethylindol-3-yl)-7-azaphthalide

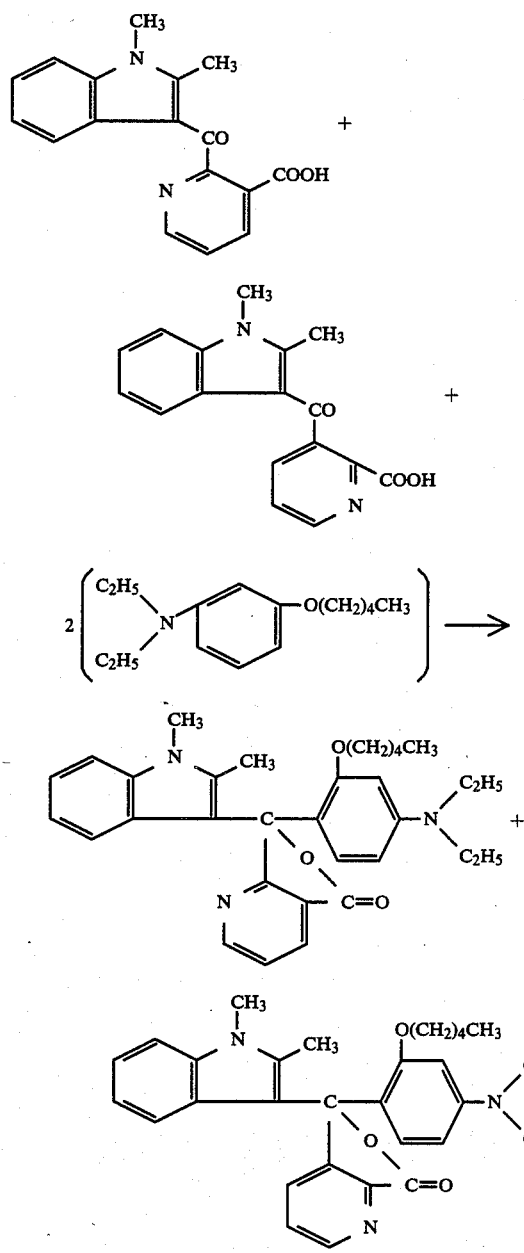

In 150 ml of acetic anhydride, 14.7 g of a mixture of (1,2-dimethylindol-3-yl) (3-carboxypyridin-2-yl) ketone and (1,2-dimethyl-3-indol-3-yl) (2-carboxypyridin-3-yl) ketone and 12.9 g of 1-n-pentyloxy-3-diethylaminobenzene were added, and the mixture was stirred for 3 hours at 65° to 70° C. After cooling the reaction mixture to room temperature, the cooled reaction mixture was poured into 1000 g of ice water and the resultant mixture was treated with toluene by the same manner as in Synthetic Example 1. As a result, 17.6 g of a mixture of 3-(4-diethylamino-2-n-pentyloxyphenyl)-3-(1,2-dimethylindol-3-yl) and 3-(4-diethylamino-2-n-pentyloxyphenyl)-3-(1,2-dimethylindol-3-yl)-7-azaphthalide was obtained as brown crystals (melting point: 163° to 169° C.). The elementary analytical data of the product were as follows.

|  | C (%) | H (%) | N (%) |
|---|---|---|---|
| Calculated | 75.12 | 7.29 | 8.21 |
| Found | 74.37 | 7.36 | 8.14 |

SYNTHETIC EXAMPLE 5

Synthesis of 3-(4-dimethylamino-2-n-pentyloxyphenyl)-3-(1-ethyl-2-methylindol-3-yl)-4-azaphthalide

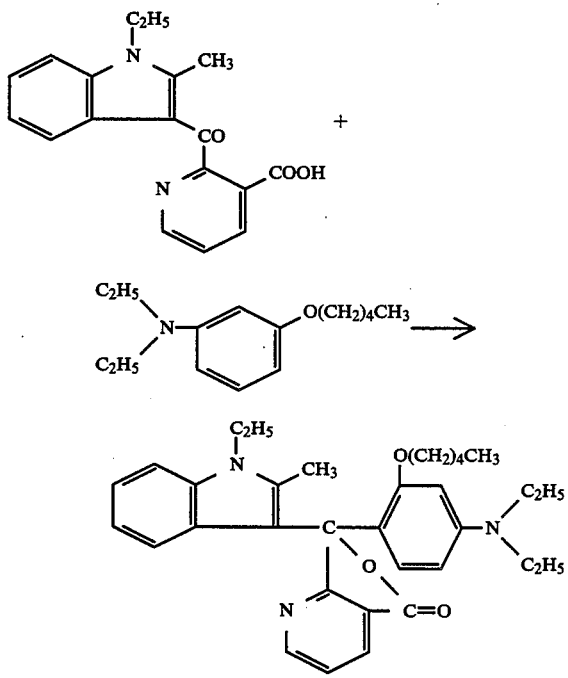

Into 75 ml of acetic anhydride, 9.2 g of (1-ethyl-2-methylindol-3-yl) (3-carboxypyridin-2-yl) ketone and 7050 g of 1-n-pentyloxy-3-dimethylaminobenzene were added, and the resultant mixture was stirred for 4 hours at 60° to 65° C. After cooling the reaction mixture to room temperature, the cooled reaction mixture was poured into 500 ml of ice water and the resultant mixture was treated with toluene and methanol by the same manner as in Synthetic Example 1. As a result, 11.9 g of the objective compound were obtained as pale blue crystals (melting point: 169° to 171° C.). The elementary analytical data of the product were as follows.

|  | C (%) | H (%) | N (%) |
|---|---|---|---|
| Calculated | 74.82 | 7.09 | 8.44 |
| Found | 75.56 | 7.03 | 8.52 |

SYNTHETIC EXAMPLE 6

Synthesis of 3-(4-dimethylamino-2-n-hexyloxyphenyl)-3-(1-ethyl-2-methylindol-3-yl)-4-azapht

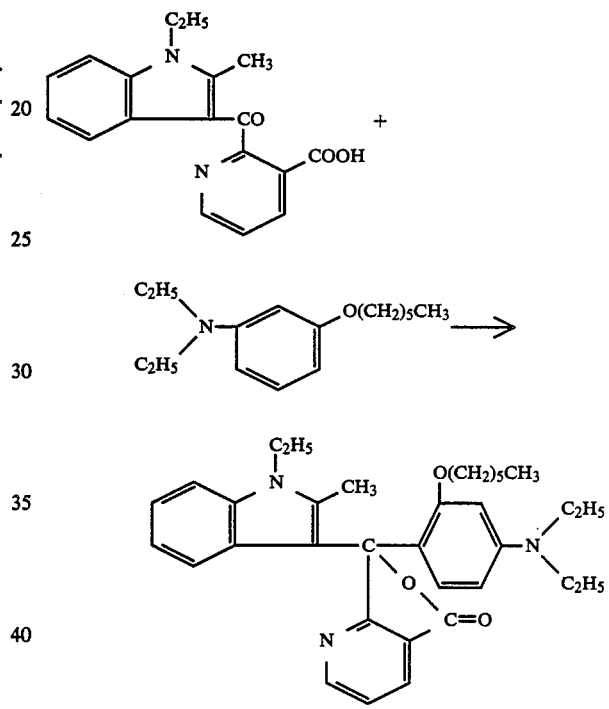

Into 40 ml of acetic anhydride, were added 6.2 g of (1-ethyl-2-methylindol-3-yl) (3-carboxypyridin-2-yl) ketone and 5.1 g of 1-n-hexyloxy-3-dimethylaminobenzene and the mixture was stirred for 3 hours at 60° to 65° C. After cooling the reaction mixture to room temperature, the cooled reaction mixture was poured into 400 g of iced water. The resulting mixture was treated with toluene and methanol by the same manner as in Synthetic Example 1 and as a result, 8.7 g of 3-(4-dimethyl-2-n-hexyloxyphenyl)-3-(1-ethyl-2-methylindol-3-yl)-4-azap melting at 127° to 129° C. was obtained as pale blue crystals. The elementary analytical data of the product were as follows.

|  | C (%) | H (%) | N (%) |
|---|---|---|---|
| Calculated | 75.12 | 7.29 | 8.21 |
| Found | 75.79 | 7.23 | 8.34 |

SYNTHETIC EXAMPLE 7

Synthesis of
3-(4-dimethylamino-2-cyclopentyloxyphenyl)-3-(1-ethyl-2-methylindol-3-yl)-4-az

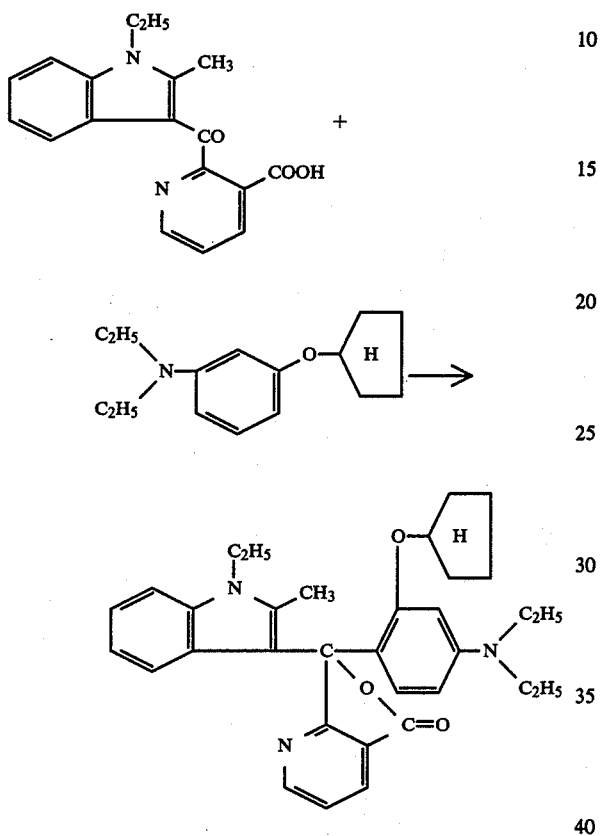

In 120 ml of acetic anhydride, 15.4 g of (1-ethyl-2-methylindol-3-yl) (3-carboxypyridin-2-yl) ket 12.5 g of 1-cyclopentyloxy-3-diethylaminobenzene were added, and the resultant mixture was stirred for 5 hours at 50° to 60° C. After cooling the mixture to room temperature, the cooled mixture was put into 1000 g of ice water to hydrolyze acetic anhydride and an aqueous dilute solution of sodium hydroxide was added to the mixture to adjust the pH thereof to 11 to 12. To the treated mixture, 200 ml of toluene were added, and after stirring the mixture under heating, the toluene layer was collected. To toluene solution, 1 g of activated carbon was added and the mixture was filtered at 80° C. and thereafter toluene was distilled off therefrom.

To the obtained solid matter, 150 ml of methanol were added and after stirring the mixture, the solid matter was collected by filtration and was dried. The object product, 3-(4-diethylamino-2-cyclopentyloxyphenyl)-3-(1-ethyl-2-methylindol-3-yl)-4-azaphthalide was obtained as pale blue crystals in yield of 21.5 g (melting point: 120° to 125° C.).

SYNTHETIC EXAMPLE 8

Synthesis of a mixture of
3-(4-diethylamino-2-cyclohexyloxyphenyl)-3-(1-ethyl-2-methylindol-3-yl)-4-azaphthalide and
3-(4-diethylamino-2-cyc-3-(1-ethyl-2-methylindol-3-yl)-7-azaphthalide

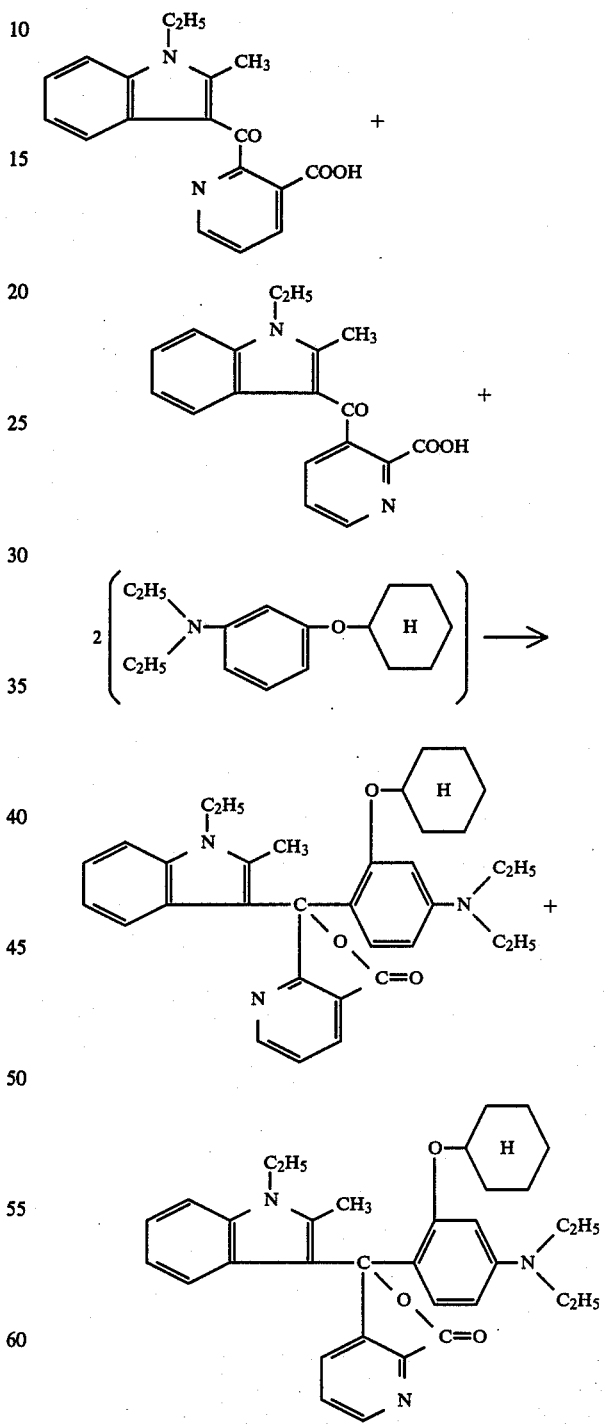

By the same procedures as in Synthetic Example 7 except for using 15.4 g of an equimolar mixture of (1-ethyl- 2-methylindol-3-yl) (3-carboxypyridin-2-yl) ketone and (1-ethyl-2-methylindol-3-yl) (2-carboxypyridin-3-yl) ketone and 13.3 g of 1-cyclohexyloxy-3-diethylaminobenzene instead of the reactants in Synthetic Example 7, an equimolar mixture of 3-(4-diethylamino-2-cyclohexyloxyphenyl)-3-(1-ethyl-2-methylindol-3-yl)-4-azaphthalide and 3-(4-diethylamino-2-cyclohexyloxyphenyl)-3-yl)-7-azaphthalide was obtained as colourless crystals in a yield of 19.7 g (melting point: 145° to 149° C.).

SYNTHETIC EXAMPLE 9

Synthesis of 3-(4-diethylamino-2-cyclohexyloxyphenyl)-3-(1,2-dimethylindol-3-yl)-4-azaphthalide

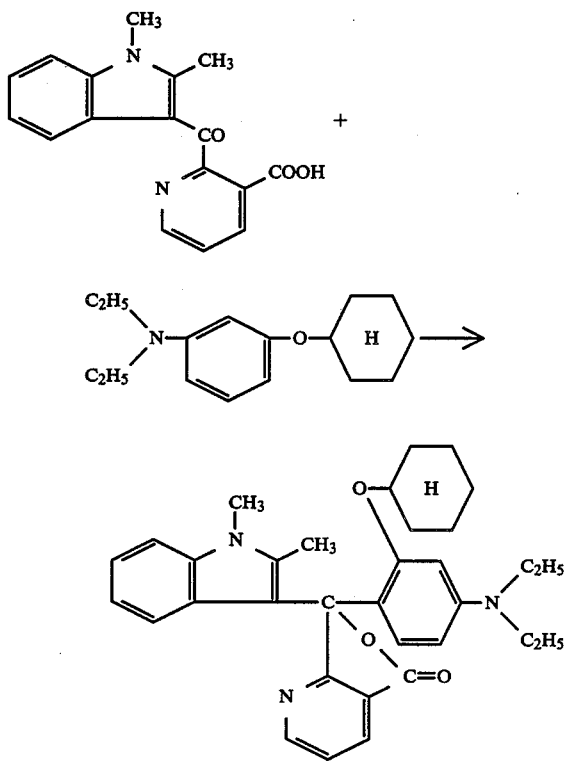

Into 150 ml of acetic anhydride, 14.7 g of (1,2-dimethylindol-3-yl) (3-carboxypyridin-2-yl) ketone and 13.3 g of 1-cyclohexyloxy-3-diethylaminobenzene were added and the resultant mixture was stirred for 3 hours at 60° to 65° C. After cooling the reaction mixture to room temperature, the cooled mixture was treated by the same procedures as in Synthetic Example 7 and 19.7 g of the object compound was obtained as pale blue crystals (melting point: 161° to 165° C.).

In the case where the pressure-sensitive copying papers are prepared by using one of the synthesized azaphthalide compounds, the known method may be used, for instance, the method of coacervation disclosed in U.S. Pat. Nos. 2,800,458 and 2,806,457 may be adopted.

In addition, also in the case where the heat sensitive recording papers are prepared, a publicly known method, for instance, the method disclosed in Japanese Patent Publication No. 14039/1970, may be adopted.

The present invention will be concretely explained while referring to the following non-limitative Preparation Examples, "part" therein meaning "part by weight":

PREPARATION EXAMPLE 1

Preparation of a Pressure-Sensitive Copying Paper

In 93 parts of monoisopropylbiphenyl, 7 parts of 3-(4-diethylamino-2-n-pentyloxyphenyl)-3-(1-ethyl-2-methyl-3-indolyl)-4-azaphthalide which had been obtained in Synthetic Example 1 were dissolved, and a solution prepared by dissolving 24 parts of gelatin and 24 parts of gum arabic in 400 parts of water and adjusted to the pH thereof to 7 was added to the prepared solution, and the mixture was emulsified by a homogenizer. After adding 1000 parts of warm water to the emulsion and stirring the mixture for 30 min at 50° C., about 1 part of an aqueous 10% solution of sodium hydroxide was added to the mixture and the whole mixture was further stirred for 30 min at 50° C. Then, dilute acetic acid was slowly added to the mixture to adjust the pH thereof to 4.5. After stirring the mixture for about one hour at 50° C., the mixture was cooled to 0° to 5° C. and further stirred for 30 min. Into the mixture, 35 parts of an aqueous 4% solution of glutaric dialdehyde were slowly added to harden the capsules and thereafter, the pH of the mixture was adjusted to 6 by an aqueous dilute solution of sodium hydroxide. By stirring the mixture for a few hours, the capsulation was completed. No colouring phenomenon was observed during the above-mentioned operation. The prepared capsulated liquid was uniformly coated on a sheet of paper and by drying the coated paper, a sheet of coated paper (the upper layer) was obtained.

By piling a lower layer prepared by coating a phenol-formaldehyde resin as the color developer on a sheet of paper onto the upper layer, a pressure-sensitive copying paper was prepared. By writing letters on the upper layer, the letters dark blue in color appeared on the lower layer instantly. The letter image showed excellent light-stability and moisture-proofness.

In addition, the capsulated surface of the upper layer showed an excellent light-stability, not exhibiting discoloration and reduction of color forming ability by exposure to sunlight.

PREPARATION EXAMPLE 2

Preparation of a Heat-Sensitive Recording Paper

Component A was prepared by mixing and pulverizing 30 parts of the product of Synthetic Example 2, namely, the mixture of 3-(4-diethylamino-2-isopentyloxyphenyl)-3-(1-ethyl-2-methyl-3-indolyl)-4-azaphthalide and 3-(4-diethylamino-2-isopentyloxyphenyl)-3-(1-eth 7-azaphthalide, 150 parts of an aqueous 10% solution of polyvinyl alcohol and 65 parts of water in a ball-mill for 10 hours. The diameter of particles of the color former after pulverizing was 3 to 5 microns.

On the other hand, Component B was prepared by mixing and pulverizing 35 parts of bisphenol, 150 parts of an aqueous 10% solution of polyvinyl alcohol and 65 parts of water in a ball-mill until the diameter of particles of the color developer became 3 to 5 microns.

A mixture of 3 parts of Component A and 67 parts of Component B was prepared and the mixture was coated onto a sheet of fine paper by a wire-bar so as to have a weight of solid matter on the sheet after drying of 7 g/m² and by drying the coated paper, a heat-sensitive recording paper was obtained. The obtained sheet of heat-sensitive recording paper was purely white in color without any fog and by heating with a heated pen, the sheet exhibited blue color instantly, and the color image showed a strong light-stability. In addition, no coloring was observed even after exposing the coated surface to sunlight.

PREPARATION EXAMPLE 3

Preparation of a Heat-Sensitive Recording Paper

In a same process as in Preparation Example 2 except for using as a color former a mixture of 10 parts of 3-(4-diethylamino-2-n-pentyloxyphenyl)-3-(1-ethyl-2-methyl-3-indolyl)-4-azaphthalide of Synthetic Example 1, 10 parts of 3-(4-diethylamino-2-n-hexyloxyphenyl)-3-(1-ethyl-2-methyl-3-indolyl)-4-azaphthalide of Synthetic Example 3 and 10 parts of crystalviolet lactone, a sheet of heat-sensitive recording paper was obtained.

The obtained heat-sensitive recording paper was pure white in color without any fog and showed the dark blue color image by writing with a heated pen instantly, and the color image showed strong light-resistance and moisture-proofness.

PREPARATION EXAMPLE 4

Preparation of a Pressure-Sensitive Copying Paper

In the same procedures as in Preparation Example 1, except for dissolving 7 parts by weight of the mixture of 3-(4-diethylamino-2-cyclohexyloxyphenyl)-3-(1-ethyl-2-methylindol-3-yl)-4-azaphthalide and 3-(4-diethylamino-2 -cyclohexyloxyphenyl)-3-(1-ethyl-2-methylindol-3-yl)-7-azaphthalide, which had been obtained in Synthetic Example 8 instead of dissolving 7 parts by weight of 3-(4-diethylamino-2-n-pentyloxyphenyl)-3-(1-ethyl-2-methylindol-3-yl)-4-azaphthalide in 93 parts by weight of monoisopropy a pressure-sensitive copying paper was prepared.

The quality and the performance of the prepared pressure-sensitive copying paper were quite the same as those of the pressure-sensitive copying paper prepared in Preparation Example 1.

PREPARATION EXAMPLE 5

Preparation of a Heat-Sensitive Copying Paper

In the same procedures as in Preparation Example 2, except for using 30 parts by weight of the mixture of 3-(4-diethylamino-2-cyclohexyloxyphenyl)-3-(1-ethyl-2-methylindol-3-yl)-4-azaphthalide and 3-(4-diethylamino-2-cyclohexyloxphenyl)-3-(1-ethyl-2-methylindol-3-which had been obtained in Synthetic Example 8, instead of 30 parts of the mixture obtained in Synthetic Example 2, a heat-sensitive copying paper was prepared. The quality and the performance of the prepared heat-sensitive copying paper were quite the same as those of the heat-sensitive copying paper prepared in Preparation Example 2.

PREPARATION EXAMPLE 6

Preparation of a Heat-Sensitive Copying Paper

In the same procedures as in Preparation Example 2, except for using a mixture of 10 parts by weight of 3-(4-diethylamino-2-cyclopentyloxyphenyl)-3-(1-ethyl-2-methylindol-3-yl)-4-azaphthalide obtained in Synthetic Example 7, 10 parts by weight of 3-(4-diethylamino-2-cyclohexyloxyphenyl)-3-(1,2-dimethylindol-3-yl)-4-azaphthalide obtained in Synthetic Example 9 and 10 parts by weight of crystalviolet lactone as a color former, a heat-sensitive copying paper was prepared. The quality and the performance of the thus prepared heat-sensitive copying paper were quite the same as those of the heat-sensitive copying paper prepared in Preparation Example 2.

What is claimed is:

1. A chromogenic compound of the formula

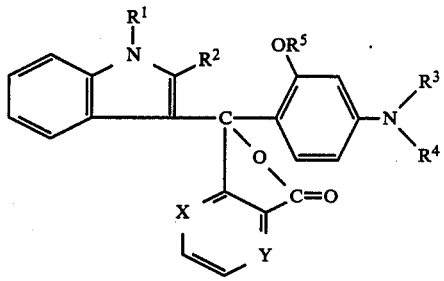

wherein $R^1$, $R^2$, $R^3$ and $R^4$ respectively represent an alkyl group having 1 to 4 carbon atoms; $R^5$ represents an alkyl group having 5 to 8 carbon atoms or a cycloalkyl group having 5 to 7 carbon atoms; one of X and Y represents a nitrogen atom and the other of X and Y represents a carbon atom.

2. A chromogenic compound according to claim 1, which comprises 3-(4-diethylamino-2-n-pentyloxyphenyl)-3-(1-ethyl-2-methylindol-3-yl)-4-azaphthalide.

3. A chromogenic compound according to claim 1, which comprises 3-(4-diethylamino-2-n-hexyloxyphenyl)-3-(1-ethyl-2-methylindol-3-yl)-4-azaphthalide.

4. A chromogenic compound according to claim 1, which comprises 3-(4-dimethylamino-2-n-pentyloxyphenyl)-3-(1-ethyl-2-methylindol-3-yl)-4-azaphthalide.

5. A chromogenic compound according to claim 1, which comprises 3-(4-dimethylamino-2-n-hexyloxyphenyl)-3-(1-ethyl-2-methylindol-3-yl)-4-azaphthalide.

6. A chromogenic compound according to claim 1, which comprises 3-(4-diethylamino-2-cyclopentyloxyphenyl)-3-(1-ethyl-2-methylindol-3-yl)-4-aza 7. A chromogenic compound according to claim 1, which comprises 3-(4-diethylamino-2-cyclohexyloxyphenyl)-3-(1-ethyl-2-methylindol-3-yl)-4-azaph 8. A color-forming recording composition comprising as a color-former at least one chromogenic azaphthalide compound represented by the formula:

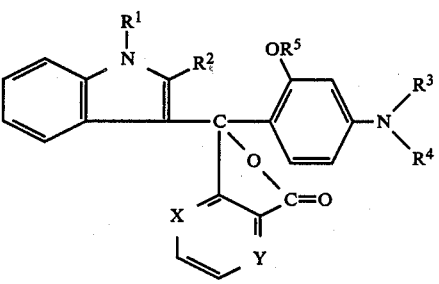

wherein $R^1$, $R^2$, $R^3$ and $R^4$ represent, respectively an alkyl group of 1 to 4 carbon atoms; $R^5$ represents an alkyl group of 5 to 8 carbon atoms or a cycloalkyl group of 5 to 7 carbon atoms; one of X and Y represents nitrogen atom and the other of X and Y represents carbon atom.

9. A composition according to claim 8, wherein the chromogenic compound is 3-(4-diethylamino-2-n-pentyloxyphenyl)-3-(1-ethyl-2-methylindol-3-yl)-4-azaphthalide.

10. A composition according to claim 8, wherein the chromogenic compound is a mixture of 3-(4-diethylamino2-iso-pentyloxyphenyl)-3-(1-ethyl-2-methylindol-3-yl)-4-azaphthalide and 3-(4-diethylamino-2-iso-pentyloxyphenyl)-3 -(1-ethyl-2-methylindol-3-yl)-7-azaphthalide.

11. A composition according to claim 8, wherein the chromogenic compound is 3-(4-diethylamino-2-n-hexyloxyphenyl)-3-(1-ethyl-2-methylindol-3-yl)-4

12. A composition according to claim 8, wherein the chromogenic compound is a mixture of 3-(4-diethylamino-2-n-pentyloxyphenyl)-3-(1,2-dimethylindol-3-yl)-4-azaphthalide and 3-(4-diethylamino-2-n-pentyloxyphenyl)-3-(1,2-dimethylindol-3-yl)-7-azaphthalide.

13. A composition according to claim 8, wherein the chromogenic compound is 3-(4-dimethylamino-2-n-pentyloxyphenyl)-3-(1-ethyl-2-methylindol-3-yl)-

14. A composition according to claim 8, wherein the chromogenic compound is 3-(4-dimethylamino-2-n-hexyloxyphenyl)-3-(1-ethyl-2-methylindol-3-yl)-

15. A composition according to claim 8, wherein the chromogenic compound is 3-(4-diethylamino-2-cyclopentyloxyphenyl)-3-(1-ethyl-2-methylindol-3-yl)-

16. A composition according to claim 8, wherein the chromogenic compound is a mixture of 3-(4-diethylamino-2-cyclohexyloxyphenyl)-3-(1-ethyl-2-methylindol-3-yl)-4-azaphthalide and 3-(4-diethylamino-2-cyclohexyloxyphenyl)-3-(1-ethyl-2-methylindol-3-yl)-7-azaphthalide.

17. A composition according to claim 8, wherein the chromogenic compound is 3-(4-diethylamino-2-cyclohexyloxyphenyl)-3-(1,2-dimethylindol-3-yl)-4-aza

* * * * *